United States Patent [19]

Richelsoph et al.

[11] Patent Number: 5,282,805
[45] Date of Patent: Feb. 1, 1994

[54] CONTROLLED FORCE MALLET

[75] Inventors: Marc E. Richelsoph, Memphis; Kenneth W. Russell, Bartlett, both of Tenn.

[73] Assignee: Dow Corning Wright Corporation, Arlington, Tenn.

[21] Appl. No.: 815,298

[22] Filed: Dec. 27, 1991

[51] Int. Cl.⁵ .............................................. A61F 2/32
[52] U.S. Cl. ...................................... 606/99; 606/100
[58] Field of Search ............... 606/75, 100, 99, 101, 606/104

[56] References Cited

U.S. PATENT DOCUMENTS

| | | | |
|---|---|---|---|
| 2,421,354 | 5/1947 | Reiter | 606/100 |
| 2,437,014 | 3/1948 | Arnesen | 606/100 |
| 2,655,921 | 10/1953 | Haboush | 606/100 |
| 2,725,878 | 12/1955 | Reiter | 606/100 |
| 3,604,487 | 9/1971 | Gilbert | 606/104 |
| 3,626,935 | 12/1971 | Pollock | 606/100 |
| 4,140,111 | 2/1979 | Morrill | 606/104 |
| 4,298,074 | 11/1981 | Mattchen | 606/104 |
| 4,476,861 | 10/1984 | Dimakos | 606/100 |
| 4,549,319 | 10/1985 | Meyer | 623/22 |
| 4,901,712 | 2/1990 | Voegell | 606/75 |
| 5,029,496 | 7/1992 | Catania | 81/22 |

Primary Examiner—Robert A. Hafer
Assistant Examiner—Michael Brown
Attorney, Agent, or Firm—John L. Chiatalas

[57] ABSTRACT

According to the invention there is provided surgical instrumentation for implanting an orthopedic prosthesis comprising a handle having opposed longitudinal ends and a head assembly situated at one end of the handle. The head assembly includes an external impact surface for transmitting force to an orthopedic instrument or prosthesis. A spring and sliding shaft arrangement are disposed within the head assembly for dampening the force from the impact surface. The head assembly is adjustable for varying the force absorbed by the spring and sliding shaft arrangement.

11 Claims, 2 Drawing Sheets

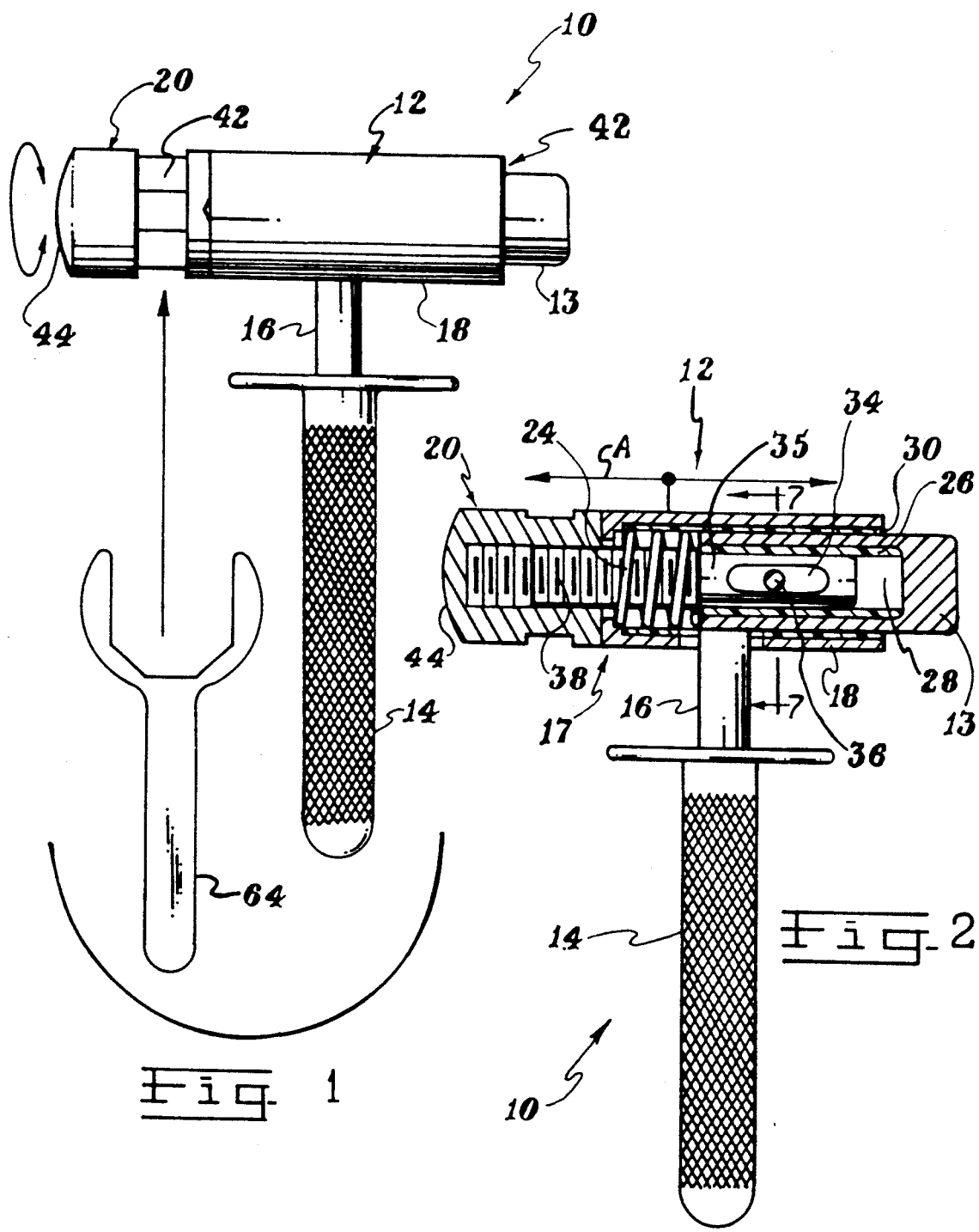

CONTROLLED FORCE MALLET

BACKGROUND OF THE INVENTION

This invention relates to surgical instrumentation for implanting an orthopedic prosthesis and, more particularly, to a force-controlled member which selectively absorbs and transmits impact forces on the member.

DESCRIPTION OF THE PRIOR ART

During surgical implantation of, for example, a hip prosthesis, it is typically necessary to utilize some type of driving tool for broaching the medullary canal, to prepare the canal to receive the prosthesis, and to drive the prosthesis fully into the canal.

Prior to insertion, the femoral canal is reamed and rasped to form a bone cavity for receiving the stem of the hip prosthesis. The rasp and prosthesis sizes are specifically matched by design, resulting in an extremely tight fit of the prosthesis in the femoral canal which lends stability to the prosthesis in the canal.

The prosthesis is typically seated in the broached femoral canal using hand pressure only. Subsequently, a mallet is used to fully seat the prosthesis, each blow of the mallet driving the stem of the prosthesis deeper into the femora canal. In using the mallet, impact forces from the mallet driving the prosthesis are a random function of the amount of force applied to the mallet by the surgeon. A disadvantage of this procedure is that there is a risk of fracturing the femur with the mallet if the prosthesis impinges along the cortical wall of the proximal femur. There is a similar risk of traumatizing the medullary canal by applying too much force to the rasp in broaching the canal.

Accordingly, there remains a need for an instrument having means for selectively controlling the impact force a prosthesis or rasp receives, thereby reducing the risk of trauma to the femur, via fracture or otherwise, during implantation of the prosthesis in the medullary canal.

SUMMARY OF THE INVENTION

According to the invention there is provided surgical instrumentation for implanting an orthopedic prosthesis comprising a handle having opposed longitudinal ends and a head assembly situated at one end of the handle. The head assembly includes an external impact surface for transmitting force to a member juxtaposed with the surface. Means are disposed within the head assembly for dampening the force from the impact surface.

An advantage of the invention is the surgeon can prelimit the force the prosthesis or driven instrument, such as a rasp, will be subjected to depending on the condition of the cortical wall of the proximal femur, thus minimizing the risk of fracturing the femur.

BRIEF DESCRIPTION OF THE DRAWINGS

The invention may be better appreciated by reference to the attached Drawings, which illustrate one or more preferred embodiments, wherein:

FIG. 1 is an external view showing the preferred mallet and a wrench for adjusting the dampening means of the invention;

FIG. 2 is an internal view partially cross sectioned, showing the head assembly connected to the handle, according to a preferred aspect of the invention;

Figure 4:
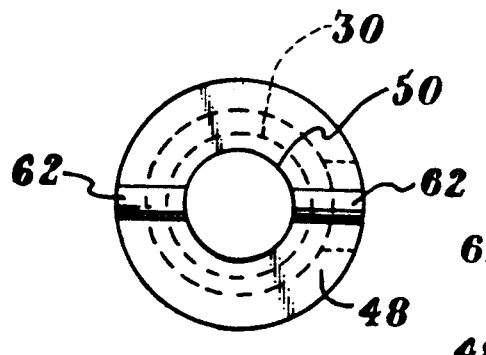
FIG. 4 is a rear view showing the collar of FIG. 4.

Further objects and advantages can be appreciated by reference to the ensuing Detailed Description, taken in conjunction with the above-mentioned Drawings, wherein the reference numerals are used to designate corresponding structures of the Drawings.

DETAILED DESCRIPTION

Referring to FIGS. 1 and 2, a preferred embodiment of a force-controlled mallet for surgically implanting an orthopedic prosthesis (not shown), e.g. a hip, is generally shown at 10. As depicted in FIG. 1, the mallet 10 comprises a handle, generally indicated at 14, having opposed longitudinal ends and a neck 16, the mallet further including a head assembly which is generally indicated at 12. The handle 14 is preferably made of a surgical-grade steel that may be knurled or otherwise sculpted on its exterior surface as desired to facilitate easy grasping by the surgeon. While the handle 14 and head assembly 12 are each shown as being cylindrical, it can be appreciated that they may have any suitable cross-section. The head assembly 12 comprises a main body 13 transversely mounted to the neck 16 of the handle 14, defining a T-shaped mallet. The head assembly 12 further comprises a collar 18, slidably disposed over the main body 13, and a ratcheting end cap 20 having an external impact surface 44. The head assembly 12 is arranged to move axially with respect to the main body 13 upon impacting a prosthesis as further indicated by arrow A in FIG. 2. Disposed within the head assembly 12 is means for dampening the force transmitted by the impact surface to the prosthesis, preferably in the form of spring 24. Further means 17 are provided for adjusting the degree of force absorbed by the dampening means, and will be set forth in greater detail below.

Figure 7:
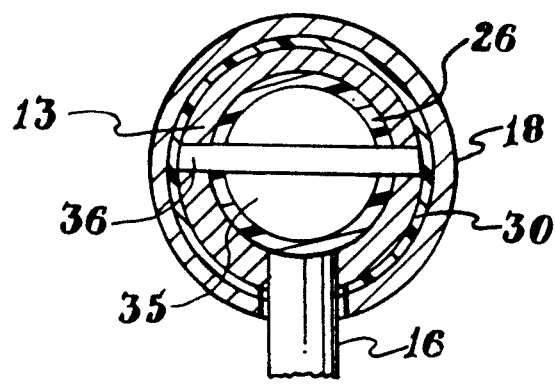
FIG. 7 is a cross sectional view of the head assembly of the mallet of FIG. 2, taken along lines 7—7.

As shown in more detail with reference to FIGS. 2 and 7, the main body 13 has a bore 28 defining a longitudinal axis extending in the direction of arrow A, including a first sleeve 26 which is axially inserted into the bore. Main body 13 is preferably made of a surgical-grade steel. The first sleeve 26 is preferably made of TEFLON® or other non-wearing surgical material. Situated within first sleeve 26 is a surgical-grade steel shaft 35 having a threaded portion 38, extending axially along the longitudinal axis of the bore 28 from the first sleeve, and a juxtaposed slotted portion 34 which is slidably coupled within the first sleeve by a rotation-limiting pin 36. The pin 36 affixes shaft 35 within bore 28 of main body 13, while permitting the shaft to travel axially the full extension of slotted portion 34 of shaft 35 while being rotationally constrained. The axial motion of shaft 35 within first sleeve 26 is analogous to reciprocation of a piston within a cylinder.

Figure 3:
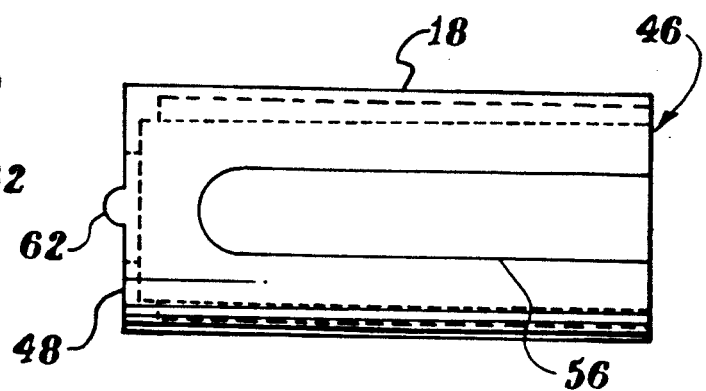
FIG. 3 is an external side elevational view showing a collar of the preferred head assembly of the invention.

Referring to FIGS. 3, 4 and 7, collar 18, preferably made of surgical-grade steel, includes an open end 46, and a bearing surface 48 having an aperture 50 and a plurality of machined protrusions 62. Collar 18 further has a longitudinally-extending first channel 56 for receiving neck 16 as the collar is slidably disposed over main body 13. The function of protrusions 62 will be described below in connection with adjustment means 17. A second sleeve 30 having a longitudinally-extending second channel (not shown) is oriented such that first channel 56 of collar 18 aligns with second channel (not shown) of the second sleeve, second sleeve 30 then being press-fitted into collar 18 to complete the assembly. Collar 18 including second sleeve 30 are both slidably disposed through open end 46 of the collar over main body 13. Second sleeve 30 is preferably made of polyethylene or other non-wearing surgical material to reduce wear by preventing metal-to-metal contact as collar 18 slides over main body 13. As collar 18 is disposed over main body 13, threaded portion 38 of shaft 35 is extendible through aperture 50 of the collar.

Figure 6:
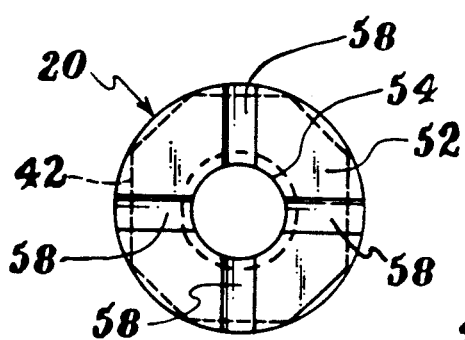
FIG. 6 is a rear view showing the ratcheting end cap of FIG. 5.
Figure 5:
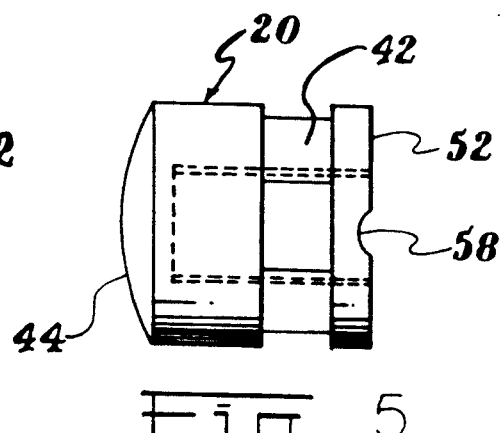
FIG. 5 is a partial side elevational view showing the preferred ratcheting end cap of the collar shown in FIGS 3–4.

Referring to FIGS. 5 and 6, the ratcheting end cap 20 further includes a bearing surface 52, opposed from the surface 44 with an internally tapped hole 54 which threadedly engages threaded portion 38 of shaft 35 as the shaft extends through aperture 50 of collar 18. Bearing surface 52 further includes a plurality of machined notches 58 that mesh with protrusions 62 of collar 18, preventing the ratcheting end cap 20 from freely rotating. Ratcheting end cap 20 is preferably made or surgical-grade steel.

The adjustment means will now be described. As shown in FIG. 1, ratcheting end cap 20 further includes a polygonal-shaped circumferential section 42 for receiving an open-ended wrench 64 used for rotating the ratcheting end cap 20 to adjust the dampening means. Surface 44 is preferably rounded providing a focal point of contact upon impact. This configuration prevents multiple impacts of the type occurring when opposing planar surfaces are unevenly impacted together.

As shown in FIG. 2, spring 24 disposed over shaft 35 is slidably coupled within bore 28 of main body 13. Spring 24 is situated over shaft 35 and seated between main body 13 and the internal portion of bearing surface 48. As described above, collar 18 is disposed over main body 13 and shaft 35, the threaded portion 38 of the shaft extending through aperture 50 of the collar and threadedly engaging tapped hole 54 of ratcheting end cap 20. Spring 24, preferably made of surgical-grade steel, functions as a shock absorber, allowing ratcheting end cap 20 and collar 18 to slide axially a predetermined amount relative to main body 13 as ratcheting end cap 20 impacts the driven surgical tool, e.g. a rasp (not shown). It is preferred that such a broaching tool have an anvil surface for receiving blows from the mallet. The inventors have found that striking an intermediate tool (not shown) is preferable to striking the prosthesis in order to avoid marring the surface or cracking of the prosthesis. The travel of head assembly 12 is dependent on the extent spring 24 is compressed between main body 13 and the internal portion of bearing surface 48. Of course, the spring constant of spring 24 can also be selected to supply a desired dampening effect.

Referring to FIGS. 1-6, collar 18 includes circumferentially-spaced protrusions 62 meshing within corresponding notches 58 formed in the end cap 20 to restrict rotation of the adjustment means 17. Spring 24 seated as described above applies a constant force that draws bearing surface 52 of end cap 20 and bearing surface 48 of collar 18 together. As the two bearing surfaces 48, 52 are drawn together, protrusions 62 mesh with notches 58, preventing end cap 20 from rotating freely. Further adjustments are made by rotating end cap 20 with a certain excess force to overcome the force of spring 24, thereby unseating protrusions 62 from within notches 58, and continuously rotating end cap 20 until the protrusions and notches again mesh, thus changing the effect of the dampening means. Notches 58 are spaced 90 degrees apart to allow adjustment means 17 to be selectively adjusted in ¼ turn increments, although various increments are possible.

In operation, end cap 20 is rotated in ¼ turn increments to compress or expand spring 24, thus changing the effect of the dampening means, clockwise rotation compresses spring 24, thereby decreasing axial travel of head assembly 12 as impact surface 44 strikes an object. As end cap 20 is rotated counter-clockwise spring 24 is expanded, thereby increasing axial travel of head assembly 12 as impact surface 44 strikes an object. It is understood that the amount of energy transmitted to the object is a function of the amount of energy spring 24 is capable of absorbing, which is further dependent upon the initial compression of the spring. It is further understood that as spring 24 is expanded, head assembly 12 has a greater ability to absorb energy and a lesser ability to absorb energy as the spring is compressed.

Prior to broaching the canal and seating the prosthesis, the surgeon has the ability to adjust the dampening means to accommodate the desired impact force to be delivered directly to the rasp or indirectly to the prosthesis, according to the structural characteristics of the prepared femoral canal or prosthesis, respectively.

Those skilled in the art will readily appreciated the present invention can be used to drive a rasp for reaming the femoral canal.

In an alternate embodiment, dampening means may instead be incorporated into an instrument, such as a rasp for reaming the femoral canal. Further, the dampening means may be a dampening member such as a shock absorber or a bladder arrangement using a fluid medium.

These and other variations of the present invention may be made which fall within the scope of the appended claims even though such variations were not specifically discussed above.

That which is claimed is:

1. A surgical instrument for implanting an orthopedic prosthesis comprising:

a handle with a longitudinal axis and opposed ends;

a head assembly connected to the handle, the head assembly including a main body transversely affixed to the handle, the main body having a bore and an enclosed end;

a collar slidably disposed over the main body, the collar having a bearing surface with an aperture and an opposed open end;

a shaft having a threaded portion and a juxtaposed slotted portion, the slotted portion of the shaft slidably coupled within the bore of the main body, the threaded portion of the shaft extending through the aperture of the collar, a ratcheting end cap including an impact surface and opposed bearing surface having a tapped hole threadedly engagable with the threaded portion of the shaft; and means disposed within the head assembly for dampening the force transmitted by the impact surface, the dampening means including means for adjusting the dampening of the force.

2. The instrument of claim 1 wherein the external impact surface is rounded to provide a focused point of contact upon impact.

3. The instrument of claim 1 wherein the means for adjusting the dampening of the force transmitted by the impact surface includes a plurality of machined notches formed from the bearing surface of the ratcheting end cap and a plurality of protrusions extending from the bearing surface of the collar, wherein the protrusions mesh with the notches preventing the ratcheting end cap from freely rotating, the means being selectively rotatable.

4. A mallet for driving an instrument or orthopedic prosthesis during surgical implantation, the mallet comprising:
- a longitudinally extending handle having opposed ends;
- a head assembly extending transversely to and interconnected with the handle defining a T-shaped configuration, the head assembly including a main body with a bore and an external impact surface for driving an orthopedic prosthesis, the head assembly further includes a collar slidably disposed over the main body, the collar having a bearing surface with an aperture and an opposed open end;
- a shaft having a threaded portion and a juxtaposed slotted portion, the slotted portion of the shaft slidably coupled within the bore of the main body, the threaded portion of the shaft extending through the aperture of the collar;
- a ratcheting end cap including an impact surface and opposed bearing surface having a tapped hole threadedly engagable with the threaded portion of the shaft; and
- means disposed within the head assembly for dampening the force transmitted by the impact surface, the means includes means for adjusting the dampening of the force.

5. The mallet of claim 4 further comprising the combination of the mallet and a rasp driven by the mallet to shape the medullary canal in preparation for reviewing a prosthesis.

6. The mallet of claim 4 wherein the external impact surface is rounded to provide a focused point of contact upon impact.

7. The mallet of claim 4 wherein the ratchet head includes a polygonal-shaped circumferential section for receiving a wrench used for rotating the ratchet head.

8. The instrument of claim 4 wherein the means for dampening comprises a spring.

9. A surgical mallet for implanting an orthopedic prosthesis comprising:
- a handle with longitudinal axis and opposed ends;
- a head assembly connected to the handle, the head assembly including a main body transversely affixed to the handle, the main body having a bore and an enclosed end;
- a collar slidably disposed over the main body, the collar having a bearing surface with an aperture and an opposed open end, the bearing surface including a plurality of protrusions extending from the bearing surface of the collar;
- a shaft slidably coupled within the bore of the main body, the shaft having an threaded portion extending through the aperture of the collar;
- a ratcheting end cap including an impact surface and a bearing surface having a tapped hole threadedly engagable with the threaded portion of the shaft, the bearing surface including a plurality of machined notches formed from the bearing surface of the ratcheting end cap;
- a dampening member disposed within the head assembly for controlling the forces transmitted by the impact surface. the ratcheting end cap including the plurality of machined notches formed from the bearing surface of the ratcheting end cap and the plurality of protrusions extending from the bearing surface of the collar, wherein the protrusions mesh with the notches to adjust the dampening effect by preventing the ratcheting end cap from freely rotating, the ratcheting end cap being selectively movable.

10. The instrument of claim 9 further comprises a mallet adapted for driving and seating a femoral prosthesis or for driving a broaching tool to prepare a bone to receive the prosthesis.

11. The instrument of claim 9 wherein the mallet is adapted for impacting a broaching tool to prepare the medullary canal of the femur to receive an implantable prosthesis.

* * * * *